United States Patent [19]
White et al.

[11] Patent Number: 5,905,183
[45] Date of Patent: May 18, 1999

[54] PROCESS FOR REDUCING THE RESIDUAL CHLORIDE CONCENTRATION IN COPPER CONTAINING SOLIDS

[75] Inventors: Michael Lee White, Attleboro, Mass.; Matthew David Butts; David Cheney DeMoulpied, both of Clifton Park, N.Y.

[73] Assignee: General Electric Company, Schenectady, N.Y.

[21] Appl. No.: 08/868,326

[22] Filed: Jun. 3, 1997

[51] Int. Cl.$^6$ ............................. A61B 1/00; C01B 33/12; C01B 7/07; B01D 21/00

[52] U.S. Cl. ..................... 588/248; 588/248; 423/336; 423/488; 210/710; 210/749; 210/751

[58] Field of Search ............................. 588/248; 423/336, 423/488; 210/710, 749, 751

[56] References Cited

U.S. PATENT DOCUMENTS

| | | | |
|---|---|---|---|
| 2,380,995 | 8/1945 | Rechew | 260/607 |
| 4,221,691 | 9/1980 | Danielson et al. | 260/336 |
| 4,393,229 | 7/1983 | Ritzer et al. | 556/430 |
| 4,408,030 | 10/1983 | Marko | 528/10 |
| 4,690,810 | 9/1987 | Breneman et al. | 423/335 |
| 4,758,352 | 7/1988 | Feldner et al. | 210/719 |
| 4,960,523 | 10/1990 | Degen et al. | 210/721 |
| 5,066,472 | 11/1991 | Ruff et al. | 423/342 |
| 5,175,329 | 12/1992 | Bokerman et al. | 556/467 |
| 5,182,095 | 1/1993 | Ruff et al. | 423/659 |
| 5,246,682 | 9/1993 | Ruff et al. | |
| 5,252,307 | 10/1993 | Ruff | 423/342 |
| 5,288,892 | 2/1994 | Pachaly et al. | 556/466 |
| 5,292,909 | 3/1994 | Chadwick et al. | 556/468 |
| 5,326,896 | 7/1994 | Chadwick et al. | 556/466 |
| 5,374,310 | 12/1994 | Bunce et al. | 106/739 |

FOREIGN PATENT DOCUMENTS

| | | |
|---|---|---|
| 3523541 | 1/1987 | Germany . |
| 3523543 | 1/1987 | Germany . |
| 3642285 | 6/1988 | Germany . |
| 3712125 | 10/1988 | Germany . |
| 3742614 | 6/1989 | Germany . |
| 3829582 | 3/1990 | Germany . |
| 0289 418 | 5/1991 | Germany . |

OTHER PUBLICATIONS

Laroze & Gilbert, Silicone for the Chemical Industry III, (1996), "New Catalytic Process for the Cleavage of Disilanes".

*Primary Examiner*—Gary P. Straub
*Assistant Examiner*—Cam N. Nguyen
*Attorney, Agent, or Firm*—Noreen C. Johnson; Douglas E. Stoner

[57] ABSTRACT

The instant invention provides a process for reducing chloride content from by-products generated during production of methylchlorosilanes, comprising, (a) hydrolyzing the by-products by combining the by-products with an aqueous medium, the aqueous medium optionally comprising a surfactant, at a pH of at least about 7 and at a temperature above about 0° C. to yield a first phase comprising essentially solids and a second phase comprising an aqueous phase; (b) separating the first and second phase; and (c) oxidizing the solids from the first phase at a temperature of at least about 300° C. for up to about 24 hours to yield a residue comprising less than about 1% by weight of chloride. The solids from the first phase may alternatively be reduced under a hydrogen flow, at a temperature of at least about 500° C. for up to about 24 hours.

10 Claims, No Drawings

PROCESS FOR REDUCING THE RESIDUAL CHLORIDE CONCENTRATION IN COPPER CONTAINING SOLIDS

FIELD OF THE INVENTION

The instant invention relates to a novel process for reducing the chloride content from selected by-products resulting from the manufacture of methyl chlorosilanes.

BACKGROUND OF THE INVENTION

The present invention relates to the treatement of by-products generated during the manufacture of methyl chlorosilanes. The basic process for the manufacture of such silane compounds is well known and is described in U.S. Pat. No. 2,380,995. Such a process generates by-products which at the present time have little or no commercial value. These by-products can present problems in their safe and environmentally acceptable ultimate disposal. The by-product streams of immediate interest are those consisting of high-boiling liquids (>75° C.); suspended silicon powder; elevated levels of copper, zinc and tin; as well as, a variety of other metals. Upon uncontrolled exposure to moisture and air, these materials may be easily ignited and/or form strong acid mists and liquid streams.

Procedures for the disposal of these by-products, and similar ones, are reported in U.S. Pat. Nos. 4,221,691; 4,408,030; 4,758,352; and 4,960,523; and in German patent DE3523541 A1.

U.S. Pat. No. 4,221,691 discloses a method of hydrolyzing polyfunctional chlorosilicon compositions which involves adding a hydrocarbon oil to the chlorosilicon composition, prior to hydrolysis in an aqueous medium containing concentrated HCl and/or $CaCl_2$. Hydrolysis of the comparable streams from the methylchlorosilane process is also disclosed in U.S. Pat. No. 4,408,030. This process utilizes concentrated HCl to hydrolyze the waste stream containing silicon chlorides. The other patents disclose similar processes but do not address the reduction of the chloride content or the disposition of copper present in the original by-product stream.

There is thus a need to develop a better process that can reduce the chloride content from the hydrolyzed by-products to produce a solid material containing copper and other metals. Among other benefits, such a product has value as a source of copper for recovery. An effective process should produce a final passivated solid that has a high flash point, little or no gas evolution, non-sticky, free-flowing and non-dusting material that can be readily handled and transported.

SUMMARY OF THE INVENTION

The instant invention provides a process for reducing chloride content from by-products generated during production of methylchlorosilanes, comprising, (a) hydrolyzing the by-products by combining the by-products with an aqueous medium, the aqueous medium optionally comprising a surfactant, at a pH of at least about 7 and at a temperature above about 0° C. to yield a first phase comprising essentially solids and a second phase comprising an aqueous phase; (b) separating the first and second phase; and (c) oxidizing the solids from the first phase at a temperature of at least about 300° C. for up to about 24 hours to yield a residue comprising up to about 1% by weight of chloride. The solids from the first phase may alternatively be reduced under a flow of hydrogen, at a temperature of at least about 400° C. for up to about 12 hours.

DETAILED DESCRIPTION OF THE INVENTION

The instant invention provides a process for reducing chloride content from by-products generated during production of methylchlorosilanes, comprising, (a) hydrolyzing the by-products by combining the by-products with an aqueous medium, the aqueous medium optionally comprising a surfactant, at a pH of at least about 7 and at a temperature above about 0° C. to yield a first phase comprising essentially solids and a second phase comprising an aqueous phase; (b) separating the first and second phase; and (c) oxidizing the solids from the first phase at a temperature of at least about 300° C. for up to about 24 hours to yield a residue comprising up to about 1% by weight of chloride.

In a preferred embodiment is provided a process wherein the solids are air oxidized for at least about eighteen hours and at a temperature of at least about 300° C., the preferred temperature being about 400° C. A further preferred process of this embodiment comprises heating the solids for at least about eight hours at a temperature of at least about 500° C. A specifically preferred process comprises heating the solids for at least two hours at a temperature of about 600° C.

Another preferred embodiment provides a process wherein the solids are heated in for about one hour, two hours being preferred, at an airflow rate of about 20 Standard Cubic Feet per Hour (SCFH) at a temperature of at least about 600° C.

The instant invention also provides a process for reducing chloride content of by-products generated during production of methylchlorosilanes, comprising, (a) hydrolyzing the by-products by combining the by-products with an aqueous medium, the aqueous medium optionally comprising a surfactant, at a pH of at least about 7 and at a temperature above about 0° C. to yield a first phase comprising solids and a second phase comprising an aqueous phase; (b) separating the first and second phase; and (c) reducing the solids under hydrogen flow of up to about 25 SCFH, at a temperature of at least about 400° C. for up to about 24 hours.

A preferred embodiment of this process is one wherein the hydrogen flow is maintained at a flow rate of about 2 SCFH to about 8 SCFH. A further preferred embodiment provides a temperature of about 550° C. to about 650° C. and the heating time is up to about 12 hours. A specifically preferred embodiment is one wherein the solids are heated for up to about 2 hours at a temperature of about 600° C. to about 650° C.

The reduction or oxidation process of the instant invention can be carried in a oven or a furnace or any other suitable heating device known to one skilled in the art. Heating devices used in the examples of the instant invention included a muffle or a tube furnace. The oxidation process can be typically carried out under reduced pressure which can facilitate in maintaining lower oxidation temperatures. The oxidation process is typically carried out under a flow of air (air oxidation). Other oxidation agents and techniques known to one skilled in the art can also be used.

The reduction of the solids can be typically carried out under a flow of hydrogen. The device used in the examples was a tube furnace. A flow rate of up to about 25 SCFH enabled the quick removal of any by-products that were formed. As one skilled in the art is aware, appropriate flow of hydrogen and an appropriate temperature should be maintained to ensure safety.

The hydrolysis can be effected in a basic aqueous medium comprising a base selected from calcium hydroxide, calcium oxide, sodium oxide, sodium hydroxide, potassium oxide, potassium hydroxide, magnesium oxide, magnesium hydroxide, calcium carbonate, calcium bicarbonate, sodium carbonate, sodium bicarbonate, magnesium carbonate, and magnesium bicarbonate. Also provided by the present invention is a process wherein the basic aqueous medium contains a anionic or nonionic surfactant such as alkyloxy(polyethyleneoxypropyl-eneoxy)isopropanol (commercially sold as Tergitol® which is produced and marketed by Union Carbide Corporation), polyoxyethylene(4)lauryl ether (commercially sold as Brij 30® by ICI), and a polyoxyethylene alkyl alcohol (sold as Renex KB® by ICI) and chemical equivalents thereof. Nonionic surfactants are preferred.

The hydrolysis process of the instant invention can be carried out at a pH between about 7–12, the preferred pH range being 9–11. The process provided by the instant invention can be carried out at temperatures ranging from about 0° C. to at least about the boiling point of the aqueous medium, although a temperature range of 25–95° C. is a typical range for the process provided by the instant invention. A preferred temperature range for the instant process being from about 35° C. to about 95° C.

In a further preferred embodiment, the aqueous medium comprises, at least in part, filter wash liquid and/or filtrate liquid, a base such as calcium hydroxide, a surfactant selected from anionic or non-ionic surfactants such as alkyloxy(polyethyleneoxypropyleneoxy)isopropanol (commercially sold as Tergitol® which is produced and marketed by Union Carbide Corporation), polyoxyethylene(4)lauryl ether (commercially sold as Brij 30® by ICI), and a polyoxyethylene alkyl alcohol (sold as Renex KB® by ICI) and chemical equivalents thereof. Nonionic surfactants are preferred.

The compositions of the various by-product samples, generated during the manufacture of methylchlorosilanes, of the by-products utilized are summarized in Table 1. These compositions are considered typical for by-product streams, but considerable batch to batch variation can exist. For instance, the concentration of solids can vary up to about 60%, and the concentration of copper can vary up to about 15%. The liquid portion of samples may include numerous high boiling multi-functional alkylchlorosilanes, alkylchlorocarbo-silanes, alkylchlorosiloxanes and alkylchlorooligosilanes, where the alkyl substituent is predominantly methyl, although others such as ethyl, propyl, may be present. Hydrocarbons and other species may also be present in varying concentrations, but usually at low levels. These by-products also contain metals that need to be removed.

TABLE 1

SAMPLE ANALYSIS

| | Sample A | Sample B | Sample C | Sample D |
|---|---|---|---|---|
| Solids | 39% | 40% | 40% | 60% |
| Al | 1.8% | 0.98% | 1.6% | 1.5% |
| Fe | 1.6% | 1.3% | ND | 1.4% |
| Zn | 1.3% | 0.75% | 1.1% | 1.2% |
| Cu | 10.0% | 8.3% | 7.7% | 9.4% |
| Cl | 26% | 25% | 32% | 26% |

ND = Not determined

Although many compounds were identified by GC/MS in the liquid portion of the by-product samples, the primary species were oligosilanes, siloxanes, and carbosilanes, generally comprising three or more chlorine atoms, thus leading to a highly cross linked hydrolyzed structure.

The novel process of the instant invention was carried out at various temperatures. The temperature can be controlled by heating, cooling, by the rate of sample addition, or other techniques known to one skilled in the art. The reaction mixture of the instant novel process was agitated at different rates and the instant process utilized a sample to water ratio of from about 1:1 to about 1:20. Some of the reactions were carried out in closed systems which enabled measurement of the volume of hydrogen evolved.

The consolidated results for Examples 1–5 are displayed in Table 2. The copper concentration of the solid product was determined by inductive coupling plasma following microwave digestion in $HF/HNO_3$. The amount of copper (Cu) and zinc (Zn) in the filtrate were determined by inductive coupling plasma. The chlorine (Cl) content in the solid was determined by Capillary Electrophoresis following microwave digestion in NaOH or by fusion with a sodium carbonate/potassium carbonate mixture, followed by titration. The degree of "passivation" was determined by a volume displacement experiment, as described in the experimental section.

The following examples are provided to illustrate the present invention.

EXPERIMENTAL DETAILS

Volume Displacement Experimental Procedure 165 mL of 2.4% Tergitol® surfactant in water was preheated to about 90° C. in a 250 mL round bottom flask with a magnetic stir bar, by immersing in a constant temperature bath. 5.0 g of freshly hydrolyzed solid was ground with a mortar and pestle and then dumped into the flask and immediately fitted with a ground glass outlet connected to a Tygon™ tube leading to an inverted 100 mL burette filled with water. The rate and total volume of gas evolved were measured. The "passivation" results are expressed in mL of gas per g of dried sample evolved after 45 minutes. <6 mL/g is considered to be reasonably well "passivated." The composition of the gas evolved was determined to be primarily hydrogen ($H_2$), with less than 20% methane by GC/MS. <1% methane was observed for the samples with pH>7.

EXAMPLES

Example 1

1.91 kg of sample A was added in portions over 2 hours to a glass 25 L reaction flask fitted with an agitator blade containing 6 L of water and 420 g of CaO at about 22° C. Upon addition, the temperature increased to about 60±/5° C. from the exotherm of the reaction. A stirring rate of 350 RPM was utilized. After about three hours following the completion of slurry addition, the sample was vacuum filtered through medium grade filter paper and then washed with water (2×5 kg). The sample was dried by exposure to the atmosphere for about 2 days. This sample was a granular solid which was completely "passivated" after drying.

Example 2

2.01 kg of sample A was added in portions to a glass 25 L resin kettle fitted with an agitator blade containing 6 L of water and 446 g of CaO at about 22° C. Upon addition, the temperature increased to about 60±/5° C. from the exotherm of the reaction and then was maintained at that temperature using an oil bath. A stirring rate of 350 RPM was utilized. After about two hours, the sample was vacuum filtered through medium grade filter paper and then washed with four 2 L aliquots of water. The sample was dried by exposure to the atmosphere for about 2 days.

Example 3

104.4 g of sample B was added to a glass jar fitted with high torque mixer, to which was added about 265 mL of water via an addition funnel. The temperature increased to 85±/5° C. from the exotherm of the reaction and then was allowed to cool toward about 25° C. during the course of the reaction. After about twenty minutes, the sample was vacuum filtered through a medium grade paper filter on a funnel and then washed with three 100 mL aliquots of water. The resultant granular solid was then dried in a 30 torr vacuum oven at about 105° C. overnight.

Example 4

48.5 g of Sample A was added to 300 g of an aqueous solution containing 16.3 g NaOH (this corresponds to 113% of the stoichiometric amount based on the chloride content) and a small amount of the Tergitol® surfactant. The temperature was maintained at about 80–90° C. with a stirring rate of 1100 RPM. After about two hours the reaction mixture was vacuum filtered through a medium grade filter paper and then washed with two 100 g aliquots of water. The filter cake was dried under full vacuum at about 105° C. for about 15 hours.

Example 5

49.3 g of Sample A was added to 150 g of an aqueous solution containing 14.4 g NaOH (this corresponds to 99% of the stoichiometric amount based on the chloride content) and a small amount of the Tergitol® surfactant. The temperature was maintained at about 80–90° C. with a stirring rate of about 1100 RPM. After about two hours the reaction mixture was vacuum filtered through a medium grade filter paper and recovered solids were dried at about 105° C. for about 15 hours.

Example 6

To a 1 L resin kettle was added 16.5 g of $Ca(OH)_2$ followed by about 150 mL water. The mixture was heated to about 55° C. in an oil bath under high agitation (ca. 1100 rpm, maintained through out the experiment). After about 10 minutes 50 g of the mixture were added over 3 minutes by syringe. After about 2 hours at about 55–60° C., the hot mixture was filtered on a Buchner funnel. The solid was then washed with hot water (ca. 95° C., 2×250 mL). The solid was dried in a vacuum oven for 14 hours at about 85° C. The solid was then analyzed for chloride content.

Example 7

The reaction conditions were essentially the same as in Example 5 except that the reaction was carried out in an aqueous solution of the Tergitol® surfactant (4.8% by weight), and the reaction temperature was maintained at about 65° C.

Example 8

Reaction conditions were about the same as in Example 6, except that (a) 13.8 g of $Ca(OH)_2$ were added, (b) the reaction temperature was maintained at about 92° C., and (c) the reaction time was extended to about 4 hours.

Example 9

Reaction conditions were about the same as in Example 8, except that the reaction was carried out in an aqueous solution of the Brij 30® surfactant (3% by weight).

Example 10

Reaction conditions were about the same as in Example 8 except that the reaction was carried out in an aqueous solution of the Renex® KB surfactant (3% by weight).

TABLE 3

EFFECT OF ADDED SURFACTANTS ON CHLORIDE CONTENT

| Example | Added Surfactant | % Cl in hydrolyzed solid |
| --- | --- | --- |
| 6 | none | 2.5 |
| 7 | Tergitol ® | 1.03 |
| 8 | none | 1.5 |
| 9 | Brij ® 30 | 1.1 |
| 10 | Renex ® KB | 0.85 |

The above table illustrates the effect of surfactants on the amount of chloride in the hydrolyzed mixture. Thus

TABLE 2

RESULTS AND ANALYSIS

| Ex. | Amount of Base Rel. to Chloride (% Stoichiometric) | Filtrate pH | Cu in Solids (%) | Chloride in Solids (%) | Cu in Filtrate (ppm) | Zn in Filtrate (ppm) | mL/g $H_2$ | Dry* Solids Yield (%) |
| --- | --- | --- | --- | --- | --- | --- | --- | --- |
| 1 | 103 | 6.0 | 11.9 | 2.18 | ND | ND | ND | 90 |
| 2 | 108 | ND | 10.2 | 2.18 | 3 | 2 | 0 | 86 |
| 3 | 0 | <1 | 8.9 | 3.4 | 345 | 4176 | ND | ND |
| 4 | 113 | 9.8 | ND | 1.9 | <1 | <1 | 4.6 | ND |
| 5 | 100 | 4.4 | ND | 2.7 | 38 | 3200 | 5.2 | ND |

ND: Not Determined
*Dry Solids yielded: (Weight Solids/Weight Initial) × 100

Examples 5 and 7 which do not use any surfactant are left with a chloride content of 2.5% and 1.5% respectively after hydrolysis. Examples 6, 8, and 9 on the other hand contained a surfactant and the effect of the surfactant is seen by the decreased amount of chloride after hydrolysis, i.e., 0.85% to 1.1%.

As used herein, metals include zinc, aluminum, copper, tin, iron, and titanium. The term "essentially free" used herein indicates that the amount of metals present is less than about 550 ppm. Also, the term "solids" means the resulting solid, as discussed in the volume displacement experiment, which evolves less than 6 ml of hydrogen per gram of the resulting solid upon base hydrolysis. The resulting solids may also be referred to as passivated solids.

The hydrolyzed solids from all the above examples, which typically had chloride contents of 2.2 to 3.5% in the absence of a surfactant, could be oxidized or reduced by the procedure outlined below. Solids from Example 1 were used to demonstrate the oxidation/reduction process of the instant invention. The solid residue thus obtained was completely passivated. The reduction procedure carried out in an atmosphere of hydrogen did not result in a fire as a result of hydrogen combustion. It is of course known in the art that reductions carried in an atmosphere of hydrogen and at elevated temperatures run the risk of fire or explosion. It is possible to run the oxidation and reduction processes under reduced pressure and thus at a lower temperature.

Oxidation and Reduction of Hydrolyzed Slurry Solids

Examples 11–12

The hydrolyzed slurry solids from Example 1 were dried in a vacuum oven for about 3 hours at 110° C. The dry solids were weighed into a crucible and placed in a muffle furnace for about 16 hours at about 600° C. The crucible was then removed, cooled to room temperature and the chloride content of the sample after observation was determined. There was a clear and significant reduction in the chloride content after the oxidation. The results are summarized in Table 4.

TABLE 4

| Example | MCS Solids Used | % Cl Before Oxidation | % Cl After Oxidation | % Weight Loss |
| --- | --- | --- | --- | --- |
| 11 | Ex. 1 | 2.18 | 0.21 | 12.7 |
| 12 | Ex. 1-Ground to dust | 2.18 | 0.31 | 13.7 |

As can be seen from the results in Table 4, the chloride content of the hydrolyzed solids clearly reduced to levels below about 0.4% from a chloride content of about 2.18. The oxidation process thus used was effective in reducing the chloride content to a level such that the residue could be recycled for its metal content.

Examples 13–17

Approximately 5 grams of hydrolyzed MCS slurry solids from Example 1 was weighed into a crucible. The crucible was then placed in a muffle furnace preset at temperatures ranging from 300 to 600° C. The heating was continued from 1 to about 18 hours after which time the crucible was removed and cooled to room temperature. The crucible was reweighed and the change in the weight for each Example was noted. The details are tabulated in Table 5.

TABLE 5

| Ex. | Temp. (° C.) | Time (hours) | Wt. Before Oxidation | Wt. After Oxidation | % Wt. Loss | % Cl |
| --- | --- | --- | --- | --- | --- | --- |
| 13 | 600 | 1 | 5.022 | 3.962 | 21.1 | 0.3 |
| 14 | 600 | 2 | 4.931 | 3.853 | 21.9 | 0.29 |
| 15 | 600 | 5 | 4.980 | 3.891 | 21.9 | 0.21 |

TABLE 5-continued

| Ex. | Temp. (° C.) | Time (hours) | Wt. Before Oxidation | Wt. After Oxidation | % Wt. Loss | % Cl |
| --- | --- | --- | --- | --- | --- | --- |
| 16 | 600 | 10 | 5.090 | 4.060 | 20.2 | 0.25 |
| 17 | 300 | 18 | 4.927 | 4.088 | 17.0 | 0.93 |

Example 18–20

Approximately 5 grams of hydrolyzed slurry solids from example 1 were added to a tared ceramic boat and placed in a tube furnace. The sample was heated to about 600° C. under a flow of air (20 SCFH). After a certain amount of time at the set temperature the sample was removed from the furnace, weighed, and analyzed for chloride. In no experiment was combustion of the sample or gases above it observed.

Table 6 lists the results.

TABLE 6

| Example | temp (° C.) | time (h) | % wt. loss | % Cl |
| --- | --- | --- | --- | --- |
| 18 | 600 | 1 | 22.2 | 0.60 |
| 19 | 600 | 2 | 21.4 | 0.48 |
| 20 | 600 | 17 | 21.0 | 0.43 |

Example 21

The hydrolyzed MCS slurry solids from Example 1 were also reduced in an atmosphere of pure hydrogen gas in a tube furnace. The flow of hydrogen gas was maintained at about 2 Standard Cubic Feet per Hour (SCFH) and the reduction was carried out at 600° C., for 17 hours. The solid lost 34.8% of its weight during this reduction. A chloride analysis revealed that the concentration of chloride was 0.57%, while the original chloride concentration was 2.18%. Under the same conditions, heating for 2 hours led to a 33.3% weight loss leaving chloride content at 0.79%.

What is claimed is:

1. A process for reducing chloride content from by-products generated during production of methylchlorosilanes, said process comprising:
   (a) hydrolyzing, at a pH of about 7–12, said by-products by combination with a basic aqueous medium, at a temperature above about 0° C., to yield a first phase comprising essentially solids and a second aqueous phase;
   (b) separating the first and second phases; and
   (c) oxidizing the solid first phase at a temperature of at least about 300° C. for up to about 24 hours.

2. A process of claim 1 wherein the solids are heated for at least about 8 hours at a temperature of at least about 500° C.

3. A process of claim 2 wherein the solids are heated at a temperature of at least about 600° C. for at least two hours, at an air flow rate of about 20 Standard Cubic Feet per Hour (SCFH).

4. A process for reducing chloride content from by-products generated during production of methylchlorosilanes, said process comprising:
   (a) hydrolyzing, at a pH of about 7–12, said by-products by combination with a basic aqueous medium at a temperature above about 0° C., to yield a first phase comprising essentially solids and a second aqueous phase;

(b) separating the first and second phases; and (c) reducing the solid first phase under a hydrogen flow of up to about 25 standard cubic feet per hour at a temperature of at least about 400° C. for up to about 24 hours.

5. A process of claim 4 wherein the hydrogen flow is maintained at a flow rate from about 2 Standard Cubic Feet per Hour (SCFH) to about 8 SCFH.

6. A process of claim 5 wherein the temperature is from about 550° C. to about 650° C.

7. A process of claim 6 wherein the solids are heated up to about 12 hours.

8. A process of claim 7 wherein the solids are heated for up to about 2 hours at a temperature of about 600° C. to about 650° C.

9. A process according to claim 1, wherein the basic aqueous medium comprises a surfactant.

10. A process according to claim 4, wherein the basic aqueous medium comprises a surfactant.

* * * * *